United States Patent [19]

Thigpen et al.

[11] 3,957,873

[45] *May 18, 1976

[54] PERACETIC ACID OXIDATION OF AMINES TO AMINE OXIDES

[75] Inventors: Hubert H. Thigpen; Wallace E. Taylor; Arthur W. Schnizer, all of Corpus Christi, Tex.

[73] Assignee: Celanese Corporation, New York, N.Y.

[ * ] Notice: The portion of the term of this patent subsequent to Oct. 11, 1983, has been disclaimed.

[22] Filed: Sept. 24, 1971

[21] Appl. No.: 183,648

Related U.S. Application Data

[60] Division of Ser. No. 823,202, Jan. 16, 1969, abandoned, which is a division of Ser. No. 318,117, Oct. 22, 1963, Pat. No. 3,522,279, which is a continuation-in-part of Ser. No. 220,553, Aug. 30, 1962, Pat. No. 3,278,562.

[52] U.S. Cl............................. 260/576; 260/570.9; 260/583 D
[51] Int. Cl.².................. C07C 87/29; C07C 87/54
[58] Field of Search............ 260/576, 570.9, 583 D, 260/607 A

[56] References Cited
UNITED STATES PATENTS 2,169,976  8/1939  Guenther et al.................... 260/561
2,769,824  11/1956  Schneider et al............... 260/583 X

FOREIGN PATENTS OR APPLICATIONS 728,585  7/1955  United Kingdom................. 260/607
958,925  2/1957  Germany........................... 260/583

OTHER PUBLICATIONS

Wagner et al., "Synthetic Organic Chemistry", p. 801 (1953).
Cope et al., "Journal American Chemical Society", Vol. 79, pp. 964–965 (1957).

*Primary Examiner*—Lewis Gotts
*Assistant Examiner*—S. P. Williams

[57] ABSTRACT

An improved process for oxidizing an amine to the corresponding amine oxide with peracetic acid comprises carrying out the reaction in a distillation column, using as oxidant the gaseous mixture of peracetic acid and acetaldehyde resulting from the vapor-phase oxidation of acetaldehyde with oxygen. The amine is introduced in liquid form into the upper portion of the distillation column while the gaseous mixture of peracetic acid and acetaldehyde is simultaneously introduced into an intermediate location in the column. Reaction takes place within the column, with acetic acid and acetaldehyde being withdrawn as vapor from the top while a liquid comprising the amine oxide product is recovered from the base.

1 Claim, No Drawings

PERACETIC ACID OXIDATION OF AMINES TO AMINE OXIDES

This is a divisional of application Ser. No. 823,202, filed Jan. 16, 1969, now abandoned, which is a divisional of application Ser. No. 318,117, filed Oct. 22, 1963, and now issued as U.S. Pat. No. 3,522,279, which in turn is a continuation-in-part of application Ser. No. 220,553, filed Aug. 30, 1962, and now issued as U.S. Pat. No. 3,278,562.

This invention relates to the use of peracetic acid on an agent for the addition of oxygen to various organic compounds.

It has been known for a great many years that acetaldehyde can be oxidized in the vapor phase with oxygen to peracetic acid, solutions of peracetic acid in an inert solvent are commercial products which have been used as oxidizing or epoxidizing agents to epoxidize olefins as well as to manufacture other useful products.

An article recently published in Great Britain by John et al, Chemistry and Industry, Jan. 17, 1962 Page 62 ff., contains a good summary of work which has been done in this field both in the preparation and utilization of peracetic acid. This article shows that peracetic acid can be made by reaction of hydrogen peroxide and acetic acid; liquid phase oxidation of acetaldehyde to acetaldehyde monoperacetate in an inert diluent followed by decomposition of the monoperacetate while still in solution in inert diluent; and vapor phase oxidation of acetaldehyde to peracetic acid followed by recovery of the perucotic acid in inert polution by vacuum distillation in the presence of benzene.

John et al relate that it is very difficult to isolate the products of vapor phase oxidation of acetaldehyde but that they have accomplished this by extractive distilling in a column containing an inert diluent which column has carefully chosen reaction conditions; e.g. a base temperature less than about 80°C. The recovered product is a 25% peracetic acid solution in the inert diluent. This article goes on to state that peracetic acid had been principally regarded as an hydroxylating agent until it was discovered that epoxidations could be accomplished by the use of peracetic acid in inert solution. Still later Sworn et al in the Journal of the American Chemical Society and in several patents showed that peracetic acid in acetic acid solution was a good epoxidizing agent.

Thus, it is seen that it has been the practice in the past to manufacture peracetic acid, by whatever method is convenient; recover the thus made peroxy acid in inert solution; either store it or sell it in solution; and then utilize the thus available per acid solution as an oxidizing or epoxidizing agent in an appropriate chemical reaction.

It has now been discovered that oxidations or eroxidations can be effected utilizing an the oxidizing agent vapors containing peracetic acid and acetaldehyde. An eminently well suited source of such vapors is the product of vapor phase oxidation of acetaldehyde. This discovery makes it practical to utilize peracetic acid as an oxidizing or epoxidizing agent directly as made.

It is an object of this invention to oxidize or epoxidize by introducing the peracetic acid oxidizing or epoxidizing agent as a vapor. It is another object of this invention to provide a series of novel chemical syntheses based upon the utilization of peracetic acid produced by the vapor phase oxidation of acetaldehyde. It is a further object of this invention to utilize the product of vapor phase oxidation of acetaldehyde directly in various oxidation or epoxidation reactions without the necessity of collection, purification or isolation of the peracetic acid content thereof. It is a still further object of this invention to carry out the oxidation reactions herein described in a novel reactor. Other and additional objects will become apparent from a consideration of this entire specification.

In accord with and fulfilling these objects, this invention includes as one of its aspects, a process which comprises carrying out oxidation or epoxidation reactions utilizing a vapor containing peracetic acid as the oxidizing or epoxidizing agent. In this connection it is preferred to utilize a vapor comprising peracetic acid in admixture with a diluent which is at least inert in the vapor phase.

Where the peracetic acid containing vapor is the reaction product of vapor phase oxidation of acetaldehyde, the vapor contains as a diluent at least acetaldehyde. It is indeed surprising that even though acetaldehyde and peracetic acid react together quite readily in the liquid phase, there is substantially no reaction between these compounds in the vapor phase. It is also quite surprising that peracetic acid will selectively oxidize or epoxidize other compounds in the process of this invention without reacting to any substantial extent with acetaldehyde. This vapor is contacted with an appropriate compound directly and without the necessity of further purification, isolation or condensation to isolate peracetic acid therefrom and upon contact the peractic acid is absorbed in the compound and oxidizes, epoxidizes or in some other way adds oxygen to the compound thereby forming an oxygenated product. The oxidation product also includes acetic acid, which is the reduced form of peracetic acid, in addition to the oxygenated derivative or derivatives. This oxidation product can be recovered and/or separated as desired.

As stated above, a particularly good source of a vapor containing peracetic acid is the oxidation product of the vapor phase oxidation of acetaldehyde. This vapor comprises acetaldehyde and peracetic acid. When this vapor is utilized to oxidize or epoxidize a compound, the reaction product is acetic acid, unreacted compound and one or more oxygen addition products of said compound, as well as acetaldehyde which generally passes through the reaction environment substantially unreacted. This product is suitably separated into its valuable components with the acetaldehyde preferably being recycled to the oxygen oxidation reaction and the acetic acid being recovered as a valuable, salable product. It is of course intended that this invention shall not be limited to disposing of this product in the manner set forth above. This is the preferred disposition of products. If desired, any one or more fractions of this reaction product may be considered waste and disposed of accordingly. Any other alternative disposition may similarly be employed as desired.

According to this invention, the vapor phase oxidation of acetaldehyde to a vaporous oxidation product comprising peracetic acid in admixture with acetaldehyde can be accomplished by following the teachings of the John et al article referred to above or the teachings of U.S. Pat. No. 2,314,345 Bludworth. In accord with this invention, however, the "oxidized reaction mixture" of the Bludworth patent or similar vapor streams comprising peracetic acid are not necessarily fractionated to inolate peracetic acid as set forth in Bludworth, but rather this "reaction mass", which is the oxidation product referred to above, is directly utilized in the steps of the instant process which follow. This reaction mass comprises, as set forth above, acetaldehyde and peracetic acid and it is most surprising that in the vapor phase these two compounds do not react to any appreciable extent to form acetic acid. This vaporous reaction mass may, and often does, contain acetic acid and may in some cases contain some unreacted oxygen or "inert" gasses such as nitrogen.

Acetaldehyde oxidation in the vapor phase with oxygen can be carried out under a wide range of reaction conditions. Best results are obtained at temperatures of about 100°C, and higher, preferably about 130°C to 180°C. Also, it is preferred for best results, though not essential, to operate substantially isothermally at any given selected operating temperature. The operating pressure should be atmospheric or higher, pressures of about 15 to 30 psig being preferred. Oxygen conversion should preferably be less than 100% in order to reduce the possibility of degradative oxidation. Exceptionally fine results have been attained when an oxygen conversion of about 85 to 95% is permitted. Contact times of vaporous acetaldehyde with oxygen up to about 46 seconds have been employed which resulted in conversion efficiencies of acetaldehyde to desired products of about 95 to 100 per cent. It is preferred to permit contact times of at least about 5 seconds. The oxidising oxygen may be diluted with inert materials if desired.

It is also preferred to utilize a vapor phase oxidation reactor which has an inert surface. In this respect, application Ser. No. 6,636, filed Feb. 4, 1960 and now U.S. 3,192,256, assigned to the assignee hereof, can be considered as suitably defining reactor materials which are inert with respect to this reaction. For example, aluminum and polytetrafluoroethylene are specific materials which do not inhibit the oxidation of acetaldehyde to peracetic acid in the vapor phase, catalyse side reactions of acetaldehyde with oxygen or encourage decomposition of peracetic acid when made. In this connection, it is also preferred to provide low surface to volume ratios in the oxidation reactor in which peracetic acid is made for use in this invention.

It has been found that a particular set of operating conditions is optimum for the vapor phase oxidation of acetaldehyde to a peracetic acid product stream for use in this invention: temperature 130° to 160°C; pressure 15 to 30 psig; oxygen concentration in feed 9 mole %: nitrogen (inert) dilution up to 20%: oxygen conversion 85 to less than 100%: contact time 8 to 40 seconds: reactor surface to volume ratio at most 0.5 per centimeter: and reactor constructed of aluminum.

According to this invention, the vapor phase oxidation product including unreacted acetaldehyde leaving the vapor phase acetaldehyde oxidation reactor is suitably fed, still in the vapor phase, into contact with an organic chemical to be oxidized or epoxidized. The product of the reaction which takes place between the acetaldehyde oxidation product and the organic chemical is preferably collected or directly separated into its components and at least the oxidized or epoxidized product recovered. This invention is adapted to use for oxidizing or epoxidizing compounds usually subjected to such treatment. Good lists of such compounds are set forth in: an article by Daniel Swern which article was published in Chemical Review 45, 1–68 (1948), U.S. Pat. No. 2,785,185 - Phillips et al, U.S. Pat. No. 1,002,004 - Beavers et al, U.S. Pat. No. 2,802,800. - Sprules et al and British Pat. No. 811,046.

A particularly important aspect of this invention is the discovery that a distillation column is admirably suited to use as the vessel in which to carry out the reaction of vaporous peracetic acid with the above referred to oxidizable compound while simultaneously separating the reaction product mass into at least two major fractions, a liquid raffinate and a vaporous distillate. Location of points of reactant feed and product withdrawal from the still-reactor as well as the operating conditions of the still-reactor, including temperatures, pressures, feed rates and column design, are so adjusted that the concentration of peracetic acid decreases upwardly in the column from the feed point; the concentration of acetic acid decreases from the top to the bottom of the column; the concentration of the compound being oxidized or epoxidized decreases from the top to the bottom of the column; the concentration of the oxygenated product increases from the top to the bottom of the column; and there is little or no acetaldehyde in the liquid phase anywhere in the column. By operating a still-reactor in such manner as to accomplish these concentration gradients, the high concentration of the compound being oxidized or epoxidized in the upper sections of the column tends to encourage reaction with peracetic acid and drive this reaction toward completion; and the high concentration of peracetic acid in the lower sections of the column tend to encourage reaction with the compound being oxidized or epoxidized and drive this reaction toward completion. Since acetic acid tends to cause ring opening of oxirane (epoxide) linkages, the combination of low concentration of oxygenated compound and high concentration of acetic acid in the upper sections of the column and the combination of low acetic acid concentration and high concentration of oxygenated compound in the lower sections of the column both tend to inhibit and minimize oxygenated product degradation and loss through ring opening and hydroxylation.

The composition of the raffinate and distillate will of course vary to at least some extent with the nature of the compound being reacted. Likewise, the proportions of the components of both the raffinate and the distillate will vary with the reaction conditions and with the proportions of the reactants. It can be stated as a general proposition, however, that the vaporous distillate will be made up of predominantly acetaldehyde, acetic acid and any gases having boiling points lower than acetaldehyde, referred to as "permanent" gases, which may exist in the reaction mass. The raffinate will, as a general rule, contain the oxygen addition product of the reaction, unreacted compound, if there is any, possibly some acetic acid, and any oxidative degradation products having a boiling point which is higher than that of acetic acid. For purposes of ease of understanding, the distillate will be further considered as consisting of acetaldehyde and acetic acid and the raffinate will be considered as consisting of oxidation addition product and any unreacted compound still retained in the system. Each of the distillate and the raffinate can often be further separated into its components. Thus where the compound being oxidized has a boiling point below its decomposition temperature and is adapted to be distilled, the raffinate can be fractionated to recover unreacted compound as a distillate and the oxygen addition product or products thereof as a raffinate.

Likewise, the vaporous distillate taken from the still-reactor can be subjected to partial condensation whereby acetic acid is condensed and acetaldehyde is retained in the vapor state. Where the product of the still-reactor is thus separated, it is convenient to recycle the vaporous acetaldehyde to the vapor phase oxidation of acetaldehyde reactor and to recycle any unreacted oxidizable compound that is recovered to the still-reactor.

The still-reactor in which it is preferred to carry out oxidation or epoxidation reactions according to this invention is conveniently a distillation column which may either have plates or be packed, provided however that the materials of construction and the packing, if there is any, should be substantially inert to the reaction and to the reactants. This column can contain, e.g., about 3 to 60 plates and preferably operates at a temperature of about 60° to 150°C. at a pressure of about 50 mm HgA to atmospheric. Where a packed column is used, the packing can be Berl Saddles, Ranchig rings, helipods or other conventional shapes. Materials of construction of a still-reactor for use in this invention include halogenated polyolefins, tin, magnesium, stainless steel, aluminum, pyrex glass, titanium, tantalum and zirconium. Feed rates of peracetic acid vapor to the still-reactor are suitably up to about 1.5 equivalents per equivalent of the compound being oxidized or epoxidized. The absolute feed rate per unit of time is of course dependent upon the size of the equipment in which this process is being carried out. Thus, where compounds are being oxidized or epoxidized which have more than one reactive center, e.g., linolenic acid or cyclopentadiene, the mole ratio of peracetic acid to the compound should be based upon the number of reactive centers in the compound, e.g., the mole feed ratio of peracetic acid to cyclopentadiene will be about twice the mole feed ratio of peracetic acid to cyclohexanone.

It will be apparent from the above general discussion that the process described herein is eminently suited to continuous operation with acetaldehyde and oxygen being fed at one end of the process and oxidizable compound fed at an intermediate point in the process, and acetic acid and oxygen addition compound or compounds of the oxidizable compound or lower homologues thereof taken as the product. While continuous operation is therefore to be preferred, it is also within the scope of this invention to operate the over-all process batchwise, that is, to feed a limited quantity of acetaldehyde, oxygen and oxidizable compound and collect a limited quantity of oxygen addition product acetic acid, acetaldehyde and unreacted oxidizable compound. This invention can also be carried out in a series of kettle type reactors or cascade type reactors.

Alternatively, it is within the scope of this invention to utilize an artificially prepared vapor stream containing peracetic acid as the epoxidising or oxidising agent in sufficient proportion to act as intended. Thus, a vapor of predetermined proportions of peracetic acid and a relatively inert diluent, such as acetaldehyde, acetic acid, acetone, methyl acetate or ethyl acetate, from whatever source, can be conveniently employed in the practice of this invention. Further, the peracetic acid can be prepared by whatever process is conveniently available and used alone or mixed with an inert diluent as desired. This process has a wide range of variants and has broad applicability. It is preferred to utilize a peracetic acid-containing vapor, as the oxidising or epoxidising medium, which contains about 2 to 35 weight percent peracetic acid, preferably 5 to 20 weight percent. The oxygen oxidation of acetaldehyde to peracetic acid, as well as the utilization of a vapor containing peracetic acid as an oxidising or epoxidising agent, have been practiced with excellent results without the aid of catalysts of any kind. However, it is within the scope of this invention to utilize a catalyst or catalysts at any appropriate point in the process to improve the yields, efficiencies or both.

The reaction conditions in the still-reactor can be varied within wide limits depending upon the efficiency and yield of products desired, and depending upon the particular compound being oxidized or epoxidized. Thus the temperature can be in the range of about 65° to 150°C, at a pressure of about 50 mm HgA to atmospheric for a contact time of about 30 seconds to 2 hours. In most embodiments of this invention the reaction conditions are so chosen that substantially all the acetaldehyde that may be in the vaporous peracetic-containing feed stream remains uncondensed in the inlet zone of the still-reactor while the peracetic acid portion of the incoming stream is absorbed upon contact thereof with the compound being oxidized or epoxidized whereupon the compound and peracetic acid react.

Representative groups of compounds which are adapted to be oxidized or epoxidized according to this invention are those having boiling points higher than acetaldehyde and generally include: 1) ketones; 2) diketones: 3) aldehydes; 4) aromatics; 5) acetylenes; 6) phosphites; 7) sulfides; 8) amines; and 9) olefinic compounds. The products of oxidizing or epoxidizing compounds of these representative groups are respectively: 1) esters; 2) carboxylic acids and anhydrides or alcohols and pyruvic acid derivatives; 3) carboxylic acids; 4) dicarboxylic acids and quinone derivatives; 5) unsaturated ketones; 6) phosphates; 7) sulphoxides and sulphones; 8) hydroxyl amines or N-oxides; and 9) epoxides. It sometimes happens that compounds oxidized according to this invention are also pyrolyzed into lower homologues thereof. The term "oxygen addition products" is intended to also encompass such oxygenated lower homologues as may be produced by the practice of this invention.

It should be noted that this invention is adapted to use in the desulfurization of petroleum fractions or crudes, particularly such fractions which have little or no olefinic unsaturation. The fraction to be desulfurized is mixed with vapor phase peracetic acid and the peracetic acid reacted therewith to convert sulfides to sulfoxides and/or disulfides to sulfonic acids. The newly created materials, sulfoxides and sulfonic acids are much more readily separable from the remainder of the hydrocarbon portions of the petroleum fraction by conventional distillation and/or extraction means than were their precursors.

This invention is also well adapted to producing N-oxides (amine oxides) by the reaction of amines with peracetic acid. These amine oxides are particularly useful in detergent formulations and as dyeing assistants. Amine oxides are prepared by oxidation of amines with peracetic acid according to any of the particular aspects set forth below. Thus, the particular process applicable to each particular amine will be determined in great measure by the boiling point of the particular amine and amine oxide under consideration. For example, methyl diphenyl amine has a boiling point above 180°C. and, as set forth below, should be oxidized in a manner similar to soybean oil.

According to one aspect of this invention, oxidizable compounds, having boiling points higher than acetic acid which are oxidizable or epoxidizable to products having boiling points higher than acetic acid, are oxidized in a still-reactor by peracetic acid to such products. Oxidizable compounds treated in this aspect of this invention are generally those which are not readily distilled and are difficult to separate from oxygenated derivatives thereof by convenient distillation means. Thus in this aspect of this invention it is desirable that the reaction be driven to completion with respect to the oxidizable compound. To this end, it is desirable to provide a mole equivalent excess, on a reactive group basis, of peracetic acid. Thus it has been found desirable to provide an excess up to about 50% of peracetic acid when epoxidizing materials according to this aspect of this invention. It is of course within the spirit and scope of this invention to utilize greater than 50% excess peracetic acid if desired, however such large excesses have not been found to improve the reaction process sufficient to warrant such use. In this aspect of this invention virtually all of the excess peracetic acid which does not react in the oxidizable compound comes out of the still-reactor as distillate and reacts with acetaldehyde upon condensation to form acetic acid which is a valuable by-product.

Materials epoxidizable or oxidizable according to this aspect of this invention are those having boiling points above about 180°C. Representative compounds in in this class include benzaldehyde, phenyl hydrazone, brassidic acid and esters thereof, α-carotene, β-carotene, cholesterol, cholesteryl acetate, cholesteryl benzoate, cinnamyl alcohol, citral, citronellal, citronellol, crotonic acid and esters thereof, diisobutylene, dihydronaphthalene, elaidic acid and esters thereof, erucic acid and esters thereof, ethyl acetoacetate, furfural diacetate, 2,6-dimethyl octadiene - 6-ol (2,6), indene, α-ionone, β ionone, itaconic acid and esters thereof, limonene, linoleic acid and esters thereof, linolenic acid and esters thereof, p-menthene-1, octadecylene-1, oleic acid and esters thereof, pulegone, tetraphenyl ethylene, diphenyl sulfide, diphenyl disulfide, methionine, thianthrene, amino azobenzene, azobenzene, p-hydroxyazobenzene, chloroquinoline, dimethyl analine, p-methoxy quinoline, methyl benzyl aniline, methyl diphenyl amine, naptho phenazine, phenanthrolines (o,m,p), phenazine, quinoline, quinoxaline, methyl vinyl carbinol, diallyl ether of Bisphenol A [2,2 bis (p,p, ′allyloxy) phenyl propane] and maleic acid and esters thereof.

In one specific embodiment of this aspect of this invention, soybean oil is epoxidized by introducing liquid soybean oil into a still-reactor near the top thereof; introducing peracetic acid containing vapor at an intermediate point in the still-reactor; taking a vaporous distillate from the still-reactor of at least acetic acid; partially condensing the distillate to remove liquid acetic acid therefrom; and recovering a liquid raffinate of epoxidized soybean oil. In a preferred form of this embodiment, the vaporous distillate contains acetic acid and acetaldehyde and the distillate is partially condensed to provide liquid acetic acid and vaporous acetaldehyde. Where the peracetic acid containing vapor feed to the still-reactor is the product of vapor phase oxidation of acetaldehyde, the vapor product, acetaldehyde, of the partial condensation of the still-reactor distillate is recycled to the vapor phase acetaldehyde oxidation reaction. It is also within the scope of this aspect of this invention to totally condense the still-reactor distillate and subsequently separate the acetic acid and acetaldehyde.

This embodiment is preferably carried out in a still-reactor operating at about 65° to 150°C, at a pressure of about 50 to 760 mm Hg absolute with a contact time of about 30 seconds to 2 hours. It is preferred to utilize a continuous process with vaporous acetaldehyde and oxygen fed to an aluminum reactor in such concentration that the feed is preferably about 10% by weight oxygen or less. The reaction suitably proceeds at about 100° to 200°C, preferably 120° to 160°C. The oxidation reactor product, at a temperature of 120° to 160°C., is fed into a distillation column while liquid soybean oil or other similar oxidizable material is fed to a higher point on the same column at a temperature at 20° to 150°C. and at a feed rate of about 0.8 to 1 part by weight of oil per part of acetaldehyde feed. The vaporous distillate product is partially condensed and the liquid raffinate product is collected as set forth above.

EXAMPLE I

In one specific example of this particular embodiment, which is given by way of illustration without it in any way limiting this invention, acetaldehyde at 85°C. was fed into an aluminum reactor at a rate of 7.7 moles per hour admixed with an oxygen stream containing 5% nitrogen in a mole ratio of acetaldehyde to oxygen of 10 to 1. Soybean oil was fed to the top plate of a 45-plate distillation column which column was operated at a temperature at 100°C. at 250 mm Hg absolute pressure with the raffinate product conducted through a short stripper section (below the 45-plate column) operating at a temperature of 150°C. The weight ratio of acetaldehyde feed (to the vapor phase oxidation reaction) to soybean oil feed was 3.2 to 1. The vapor phase oxidation product containing 12 weight percent peracetic acid was fed in the vapor state below the bottom plate of the stripper section. The soybean oil reacted with the peracetic acid in the still to produce acetic acid and epoxidized soybean oil. The still-reactor raffinate was quickly cooled to room temperature as it came off from the base of the still-reactor and 107 parts by weight per hour of epoxidized soybean oil product containing 1.3% acetic acid was recovered. The acetic acid was removed by washing to yield a product containing 6.9 weight percent oxirane oxygen with an iodine number of 1.1 and a color of Gardner 1. The still-reactor distillate came off as a vapor from the top of the still at 100°C. and was passed through a dry ice-acetone trap to condense acetaldehyde and acetic acid while venting the "permanent" gasses.

In another specific embodiment of this aspect of this invention, esters of tall oil acid, such as 2-ethylhexyl tallate, are epoxidized by reacting tall oil ester with vaporous acetaldehyde oxidation product in a manner similar to that set forth above with respect to soybean oil. The reaction products are acetic acid and epoxidized tallate with acetaldehyde passing through the reaction system.

EXAMPLE II

In another specific example of this embodiment, acetaldehyde was oxidized with oxygen as set forth in Example I above to yield peracetic acid oxidation product containing vaporous acetaldehyde. 2-Ethylhexyltallate was fed into a still-reactor identical to that described in Example I above at 25°C. in a weight ratio of acetaldehyde feed to tallate feed of 3 to 1. The still-reactor raffinate came off as a liquid at room temperature to yield 116 parts by weight per hour of epoxidized 2-ethylhexyltallate containing 1.3% by weight acetic acid. The raffinate was washed to remove acetic acid yielding a product having an oxirane oxygen content of 5% by weight, an iodine number of 2 and a color of Gardner 1. The still-reactor distillate came off as a vapor at 100°C. and was condensed as set forth above in Example I.

EXAMPLE III

In another specific example of this embodiment, 90 parts by weight per hour of a solution of 34.5 weight percent peracetic acid in acetic acid was vaporized at a pressure of 250 mm Hg absolute and fed into a still reactor similar to that described in Example I between the bottom tray of the 45-tray column and the stripper section. The column was maintained at 100°C. Soybean oil was fed at 25°C. onto the top tray of the column at 69 parts by weight per hour. The epoxidized product was taken as a raffinate through the stripper section at 150°C. and was recovered at 30°C. The yield was 72 parts by weight per hour of raffinate containing 3.8 weight percent acetic acid. The raffinate was washed with dilute potassium hydroxide solution to remove the acetic acid therefrom and the resultant epoxy product after drying had an oxirane oxygen content of 6.8 weight percent and and iodine number of 1. The column distillate was taken at a rate of 86 parts by weight per hour and was acetic acid containing 4.4% by weight peracetic acid.

EXAMPLE IV

A vapor mixture, similar to that used in Example I, containing 9.9 mole % peracetic acid, 23.4 mole % acetic acid, and 66.7 mole % acetaldehyde was fed at a rate of 4.65 moles per hour into a still-reactor identical to that described in Example I, between the bottom plate and the short stripper section. 2,2-Bis(p,p'diallyloxyphenyl) propane was fed into the top of the still-reactor at a rate of 0.325 equivalents per hr. The still-reactor was maintained at 100°C. and 250 mm HgA. The epoxidized product was recovered as a raffinate which came through the stripper section of the still-reactor at 150°C., quickly cooled, and was taken from the system at 30°C. The yield was 55 parts by weight per hour of raffinate, which contained 5.7 wt % acetic acid, and which had an oxirane oxygen content of 4.3 wt %. The raffinate product was washed with dilute sodium hydroxide solution to remove the acetic acid and thus purify the product 2,2-bis (p-glycidylphenyl) propane. The distillate was taken overhead and condensed in dry ice-acetone cooled traps. The total distillate was 234 parts by weight per hour containing 137 parts by weight per hour of acetaldehyde, 11 parts by weight per hour of peracetic acid, and 86 parts by weight per hour of acetic acid.

In another aspect of this invention, compounds having boiling points from about 125° to about 180°C. are oxidized or epoxidized in a still-reactor by peracetic acid to an oxygenated derivative of the compound. Compounds treated according to this aspect of this invention are generally readily separable, by distillation techniques, from an oxygenated derivative thereof.

In this aspect of this invention it is convenient to recover any unreacted oxidizable compound and oxygenated derivative thereof as raffinate while taking acetic acid and acetaldehyde as vaporous distillate. The oxidizable compound in this aspect of this invention may suitably be maintained in the column by utilizing a high reflux or by providing a still-reactor with a large number of actual or theoretical plates or trays. Preferably acetic acid and acetaldehyde are refluxed overhead while the compound being processed is refluxed in the column. It is also preferred to provide the break point between the acetic acid and the compound being processed a few plates down from the top of the column. The level of the break point can be controlled by controlling the amount of acetic acid reflux.

Representative compounds processable according to this aspect of this invention include allyl propionate, camphene, dichloro ethylene, dicyclo pentadiene, 1-dodecene, methyl crotonate, methyl cyclohexanone, nonene-2, octylene, pinene, styrene, stilbene (cis), dibenzyl sulfide, diallyl sulfide, ethyl n-butyl sulfide, 2,5-dimethyl pyrazine, 6-nitro quinoline, nitro styrene (o,m,p) and cyclohexanone.

Suitable reaction conditions for the oxidation or epoxidation of compounds according to this aspect of this invention with vaporous acetaldehye oxidation product include a temperature of peracetic acid containing feed of 10° to 180°C.; a still reactor 110° of 100 to 760 mm Hg absolute; oxidizable compound feed rate of 0.8 to 1.2 parts by weight per part of peracetic acid feed at about 25° to 150°C.; a distillate temperature of 80° to 150°C.; a partial condenser temperature of 0° to 100°C.; and a raffinate temperature of 150° to 250°C. The oxidizable compound and the oxygenated products thereof can be separated by distillation or solvent extraction.

EXAMPLE V

In another specific embodiment of this invention, a vapor mixture, similar to that used in Example I, containing 9.2 mole % (13.4 wt %) peracetic acid, 29.2 mole % (34.0 wt %) acetic acid, and 61.7 mole % (52.6 wt %) acetaldehyde was fed at a rate of 1.85 moles per hour (95.2 parts by weight per hour) to the 15th plate from the bottom of a 50-plate column similar to that described in Example I. Cyclohexanone was fed to the 45th plate of the column at a rate of 0.71 moles per hour (70 parts by weight per hour). The column was operated at 100°C. and 135 mm HgA. Acetic acid, acetaldehyde, and a small amount of cyclohexanone were taken as a vaporous distillate through partial condensors maintained at 25°C, whereby acetic acid, cyclohexanone, and acetaldehyde were recovered. The raffinate was taken from the column base (115°C.) at a rate of 64.5 parts by weight per hour and contained 47.7 parts by weight per hour cyclohexanone, 2.0 parts by weight per hour α-hydroxycyclohexanone and 14.8 parts by weight per hour of ε-caprolactone.

In still another aspect of this invention, compounds having boiling points at most about 125°C., and preferably above about 30°C. are oxidized or epoxidized in a still-reactor by peracetic acid to an oxygenated derivative of the compound. Compounds treated according to this aspect of this invention are recovered as raffinate from the still-reactor in admixture with by-product acetic acid while any acetaldehyde which may be in the system is taken as a distillate overhead. To maintain the compound to be oxidized, and its oxidation product in the liquid phase, it is preferable to remove heat, as by heat exchangers external to each tray or by overhead reflux, during the reaction in the distillation system.

Representative compounds processible according to this aspect of this invention include allyl alcohol, diallyl ether, allyl chloride, caprylene, cycloheptene, cyclohexadiene, cyclohexene, cyclopentadiene, diallyl amine, pentene-1-Ol-3, ethylvinyl ether, heptene-, hexene-1, isoprene, methyl cyclohexene, divinyl sulfide, 5-nitroquinoline, pyridine, and allyl acetate.

EXAMPLE VI

In one specific example of the practice of this aspect of this invention, glycidyl acetate was obtained by the epoxidation of allyl acetate. A mixture of peracetic acid (28.3 weight %) and acetic acid (71.7 weight %) were fed to the 45th plate from the bottom of a 50-plate still-reactor similar to that used in Example I at a rate of 62.4 parts by weight per hour (0.23 moles per hour of peracetic acid). Allyl acetate was fed to the 15th plate of the still-reactor at a rate of 53.4 parts by weight per hour (0.55 moles per hour). The still-reactor was operated at 155 mm HgA pressure giving a still-reactor temperature of 60° – 65°C. and a base temperature of 78°C. Vaporous peracetic acid was liquified in contact with allyl acetate reacting therewith to form glycidyl acetate. The raffinate was taken from the column base at a rate of 116 parts by weight per hour containing 33.4 parts by weight per hour of allyl acetate, 15.2 parts by weight per hour of glycidyl acetate, 7.3 parts by weight per hour of glycerine diacetate, 6.4 parts by weight per hour of glycerine triacetate, and 56.7 parts by weight of acetic acid.

According to another embodiment of this aspect of this invention, the epoxidation product of allyl acetate can be hydrolyzed to glycerine. In fact, this invention encompasses the process of converting propylene glycol diacetate to glycerine and other similar reactions.

Thus, propylene glycol diacetate is readily pyrolyzed to allyl acetate, which is then epoxidized with peracetic acid to glycidyl acetate, followed by hydrolysis of the epoxidation product to glycerine with acetic acid by-product being recovered. The epoxidation product of allyl acetate is introduced into contact with 1.6 times its weight of water at 100°C. which water is 0.01 N in sulfuric acid, in order to hydrolyze the epoxidation product to glycerine. The hydrolysis product is subjected to distillation or other separation techniques to remove the acetic acid therefrom and thus recover glycerine.

Still another aspect of this invention is the oxidation or epoxidation of an organic compound capable of being oxidized or epoxidized in a distillation column with vaporous peracetic acid feed according to the process as aforesaid in the presence of an inert organic solvent for peracetic acid fed to the column (still-reactor).

Thus, it is within the scope of this aspect of this invention to feed the vaporous peracetic acid to the still-reactor as a vapor stream of peracetic acid admixed with the inert organic solvent with or without unreacted acetaldehyde and/or other minor constituents (e.g. oxygen, carbon oxides, acetic acid, etc.). It is also within the scope of this aspect of this invention to feed a vaporous peracetic acid stream to the still-reactor as aforesaid and separately and simultaneously feed the inert organic solvent as a liquid or a vapor to the still-reactor.

One particular advantage to the use of an inert organic solvent in the instant invention is that the presence of this material tends to maintain the temperature in the still-reactor lower than it would be if the solvent were not present. This tends to minimize undesirable side reactions. For example, in the oxidation of cyclohexanone to caprolactone by the process of this invention, one of the undesirable by-products of the oxidation is adipoin ($\alpha$-hydroxycyclohexanone). It has been found that the production of this by-product can be substantially reduced by the practice of this aspect of this invention.

Inert organic solvents which are generally applicable to use in this aspect of this invention do not react with either the reactants or the reaction products under the reaction conditions in the still-reactor, nor do they in any way interfere with the primarily desired reaction.

Examples of specific organic materials which are useful include acetone, methyl acetate, ethyl acetate, dioxane, etc.

EXAMPLE VII

The vapor product stream from acetaldehyde oxidation containing an estimated 0.83 moles per hour of peracetic acid, 8.29 moles per hour of unreacted acetaldehyde, 0.04 moles per hour of unreacted oxygen and small amounts of CO, $CO_2$, methane, methanol, formaldehyde, and water was fed continuously to tray 10 of a 38-tray, 2-inch Oldershaw column. Acetone at 27°C. as solvent was fed continuously also to tray 10 at a rate of 230 grams per hour and cyclohexanone was fed continuously at a rate of 95 grams (0.97 moles) per hour to tray 30. The overhead distillate from the column contained the unreacted AcH and 38 grams per hour of acetone. The noncondensable gases were vented through the overhead condenser system. The base stream, taken continuously from the termosiphon reboiler, contained 18.7 grams per hour of unreacted peracetic acid, 24 grams per hour of $\epsilon$-caprolactone, 65 per hour of unreacted cyclohexanone, 0.12 grams per hour of adipoin, 0.78 grams per hour of adipic acid, 0.13 grams per hour of nonvolatile nonacidic material and 17.6 grams per hour of acetic acid. This base stream was accumulated and heated to reflux at 70°C. for 2.0 hours to complete the conversion of peracetic acid. Careful analysis of this material indicated that 61.7 grams (0.54 moles) per hour of $\epsilon$-caprolactone, 0.29 grams (0.0025 moles) per hour of adipoin, 1.74 grams (0.012 moles) per hour of adipic acid, and 0.34 grams per hour of polymeric material was produced. This product distribution represents the following yield based on cyclohexanone converted:

| | Moles per 100 Moles of Cyclehexanone Converted |
|---|---|
| $\epsilon$-caprolactone | 96.9 |
| Adipoin | 0.4 |
| Adipic Acid | 2.1 |
| Polymer (a) | 0.5 |
| | 99.9 |

(a) Calculated on the basis of molecular weight 114 so that it represents an equivalent amount of $\epsilon$-caprolactone.

EXAMPLE VIII

Under similar conditions to those set forth in Example VII, cyclohexanone was oxidized to $\epsilon$-caprolactone in the presence of methyl acetate. The efficiencies (moles per 100 moles of cyclohexanone oxidized) were as follows:

| | |
|---|---|
| ε-caprolactone | 96.1 |
| Adipoin | 1.6 |
| Nonvolatile acid as adipic | 1.5 |
| Polymer | 0.8 |

In any or all of the aspects of this invention, it is desirable to obtain maximum utilization of peracetic acid as an oxidizing agent. In order to accomplish this, it is desirable to prevent the non-productive decomposition of peracetic acid e.g. by catalysis or thermal degradation. Certain contaminants, e.g. iron, chromium, manganese, copper, and nickel should either be excluded from the system described herein, inhibited, sequestered or in some other way prevented from catalyzing the degradation of peracetic acid. It has been found particularly effective to use aluminum as the material of construction in which this process is carried out. Of particular value for use as a construction material in this invention is grade 6061 aluminum which is a normal structural grade aluminum free of copper, manganese, cobalt, iron, nickel and other heavy metals and which is structurally strong. If possible, it is preferred to use pure aluminum as the construction material for the practice of this invention.

While this invention has been described with reference to the use of peracetic acid as an epoxidizing agent and with reference to the manufacture of peracetic acid, it should be understood that other per carboxylic acids, e.g. perpropionic acid, are also useful in this invention.

It is to be understood that the foregoing detailed description is given merely by way of illustration and that many variations may be made therein without departing from the spirit of our invention.

We claim:

1. In a process for preparing an amine oxide by reacting an amine with peracetic acid, said amine having a boiling point greater than about 180°C, the improvement which comprises:

introducing said amine in the liquid form into a distillation column at a location near the top thereof;

simultaneously introducing into an intermediate location in said column the gaseous product formed by reacting acetaldehyde and oxygen in the vapor phase to form a gaseous mixture comprising peracetic acid and unreacted acetaldehyde;

reacting said amine and said gaseous product comprising peracetic acid in said distillation column at a temperature between about 65°C and about 150°C and at a pressure of about 50 to 760 mm of mercury absolute to form said amine oxide and byproduct acetic acid;

removing a vapor comprising acetic acid and acetaldehyde from the top of said distillation column; and recovering a liquid comprising said amine oxide from the base of said column.

* * * * *

UNITED STATES PATENT AND TRADEMARK OFFICE
CERTIFICATE OF CORRECTION

PATENT NO. : 3,957,873
DATED : May 18, 1976
INVENTOR(S) : Hubert H. Thigpen, Wallace E. Taylor, Arthur W. Schnizer It is certified that error appears in the above-identified patent and that said Letters Patent are hereby corrected as shown below:

In column 1, line 16, for "to peracetic acid, solutions of peracetic acid in an inert" read -- to peracetic acid. Solutions of peracetic acid in an inert --

Column 1, line 31, for "perucotic" read -- peracetic --.

Column 1, line 32, for "pplution" read -- solution --.

Column 1, line 45, for "Sworn et al" read -- Swern et al --.

Column 1, lines 56 and 57, for "eroxidations" read -- epoxidations --

Column 2, line 65, for "2,314,345" read -- 2,314,385.

Column 3, line 1, for "inolate" read --isolate --.

Column 4, line 1, for "1,002,004" read -- 3,002,004 --.

Column 5, line 20, for "Ranchig" read -- Raschig --.

UNITED STATES PATENT OFFICE
CERTIFICATE OF CORRECTION

Patent No. 3,957,873    Dated    May 18, 1976

Inventor(s) Hubert H. Thigpen, Wallace E. Taylor, Arthur W. Schnizer

It is certified that error appears in the above-identified patent and that said Letters Patent are hereby corrected as shown below:

Column 10, line 28, for "taining feed of 10° to 180°C; a still reactor 110° of 100" read -- taining feed of 110° to 180°C; a still reactor pressure of 100 --.

Column 11, line 8, for "pentene-1-O1-3" read -- pentene-1-O1-3 -- and for "heptene" read -- heptene-1 --.

Signed and Sealed this

Twenty-fourth Day of May 1977

[SEAL]

Attest:

RUTH C. MASON
Attesting Officer

C. MARSHALL DANN
Commissioner of Patents and Trademarks